United States Patent
Kulkarni et al.

(10) Patent No.: US 11,197,817 B2
(45) Date of Patent: Dec. 14, 2021

(54) WHITENING SYSTEMS FOR HYDROPHOBIC WHITENING GELS

(71) Applicant: Colgate-Palmolive Company, New York, NY (US)

(72) Inventors: Pooja Kulkarni, Plainsboro, NE (US); Jason Nesta, Cedar Knolls, NJ (US)

(73) Assignee: Colgate-Palmolive Company, New York, NY (US)

( * ) Notice: Subject to any disclaimer, the term of this patent is extended or adjusted under 35 U.S.C. 154(b) by 591 days.

(21) Appl. No.: 15/566,230

(22) PCT Filed: Apr. 15, 2015

(86) PCT No.: PCT/US2015/025840
§ 371 (c)(1),
(2) Date: Oct. 13, 2017

(87) PCT Pub. No.: WO2016/167755
PCT Pub. Date: Oct. 20, 2016

(65) Prior Publication Data
US 2018/0092828 A1   Apr. 5, 2018

(51) Int. Cl.
*A61K 8/895* (2006.01)
*A61K 8/25* (2006.01)
*A61Q 11/00* (2006.01)
*A61K 8/22* (2006.01)

(52) U.S. Cl.
CPC ............... *A61K 8/895* (2013.01); *A61K 8/22* (2013.01); *A61K 8/25* (2013.01); *A61Q 11/00* (2013.01); *A61K 2800/31* (2013.01)

(58) Field of Classification Search
CPC . A61K 8/895; A61K 8/22; A61K 8/25; A61K 2800/31; A61Q 11/00
See application file for complete search history.

(56) References Cited

U.S. PATENT DOCUMENTS

| | | |
|---|---|---|
| 8,815,215 B2 | 8/2014 | Prencipe et al. |
| 8,921,454 B2 | 12/2014 | Schiro et al. |
| 9,023,329 B2 | 5/2015 | Bevinakatti et al. |
| 9,308,399 B2 | 4/2016 | Zaidel et al. |
| 9,744,116 B2 | 8/2017 | Bolognini et al. |
| 2006/0147394 A1 | 7/2006 | Shastry et al. |
| 2008/0044363 A1 | 2/2008 | Montgomery |
| 2010/0104519 A1 | 4/2010 | Chung et al. |
| 2010/0183534 A1* | 7/2010 | Bevinakatti ............ A61Q 1/02 424/64 |

FOREIGN PATENT DOCUMENTS

WO   2007074331   7/2007

OTHER PUBLICATIONS

International Search Report and Written Opinion of the International Searching Authority in International Application No. PCT/US2015/025840, dated Nov. 23, 2015.
An Jiaju, Dictionary of Practical Fine Chemical Engineering, China Light Industry Press, 2nd Edition, pp. 896-897 (2000).
ARES-G2 Rheometer, Technology, <http://www.tainstruments.com/pdf/literature/RH025.pdf.>.
Chen, Tianhong, "Rheological techniques for yield stress analysis," TA Instruments, pp. 1-5.

* cited by examiner

*Primary Examiner* — Adam C Milligan

(57) ABSTRACT

Disclosed herein are tooth whitening compositions comprising at least one hydrophobic polymer carrier; fumed silica; sorbitan sebacate behenate polymer; and at least one whitening agent, wherein the tooth whitening composition has a structural parameter such that G'/G" is greater than or equal to about 1. Also disclosed herein are methods of making a tooth whitening composition and methods of whitening the surface of a tooth.

20 Claims, 3 Drawing Sheets

WHITENING SYSTEMS FOR HYDROPHOBIC WHITENING GELS

BACKGROUND

Disclosed herein are thickening systems for use in hydrophobic compositions, such as hydrophobic tooth whitening compositions. In certain embodiments, the tooth whitening compositions disclosed herein may be in the form of gels.

It has become desirable for a person's teeth to appear bright or "white." Society places a high value on the "whiteness" of one's teeth. One whose teeth are white may enjoy more personal confidence and satisfaction and may even enjoy greater social acceptance.

In a mammal, a tooth is comprised of an inner dentin layer and an outer hard enamel layer that is the protective layer of the tooth. The enamel layer of a tooth is naturally an opaque white or slightly off-white color. It is the enamel layer that can become stained or discolored. The enamel layer of a tooth is composed of hydroxyapatite mineral crystals that create a somewhat porous surface. These hydroxyapatite crystals form microscopic hexagonal rods or prisms that make up the enamel surface. As a result, the surface of the enamel layer presents microscopic spaces or pores between the prisms. It is believed that this porous nature of the enamel layer is what allows staining agents and discoloring substances to permeate the enamel and discolor the tooth. These remaining substances can occupy the microscopic spaces and eventually alter the color of the tooth.

Many substances that a person confronts or comes in contact with on a daily basis can stain or reduce the whiteness of one's teeth. In particular, the foods, tobacco products, and fluids that one consumes tend to stain one's teeth. These products or substances tend to accumulate on the enamel layer of the tooth and form a pellicle film over the teeth.

These staining and discoloring substances can then permeate the enamel layer. This problem occurs gradually over many years, but imparts a noticeable discoloration of the enamel of one's teeth. So long as the discolored teeth are still healthy and do not pose any health risk or problem, a product or substance that would whiten the discolored teeth would be advantageous. It is also essential that a tooth whitening product that is to be used at home or in private by the consumer be safe and easy to use and be stable and retain its whitening efficacy during its storage on retail store shelves as well as over the period of use by the consumer.

Products and substances that are presently available to whiten teeth may include a variety of different ingredients, but the primary active ingredient is a peroxide agent formulated into a liquid, paste or gel carrier. There is a need to assist peroxide retention on the tooth surface to achieve the maximum bleaching performance. This may be achieved by incorporating the peroxide agent into an adhesive, for example a pressure sensitive adhesive that can adhere to the tooth surface. Currently, tooth whitening compositions may comprise at least one pressure sensitive adhesive, such as a silicone pressure sensitive adhesive, as well as at least one adhesion enhancing agent.

Known adhesion enhancing agents include plastics, such as, for example, a dispersion of polyethylene in mineral oil, to form a viscoelastic structure. The viscoelastic structure created in part through the use of polyethylene ensures that solid materials remain homogenously distributed in the tooth whitening composition, thereby increasing the product's shelf life and stability. Recently, however, there has been heightened consumer awareness of the use of plastics such as polyethylene in personal care products, resulting in a demand for alternative materials. Disclosed herein are suitable alternatives for polyethylene, which may be used to provide viscoelastic structure in personal care formulations, such as tooth whitening compositions.

There is a need in the art for improved tooth whitening compositions that can provide good peroxide retention on the tooth surface, whitening efficacy, and a stable formulation, while incorporating ingredients that are appealing to consumers.

BRIEF SUMMARY

Disclosed herein are tooth whitening compositions comprising at least one hydrophobic polymer carrier, fumed silica, sorbitan sebacate behenate polymer, and at least one whitening agent, wherein the tooth whitening composition has a structural parameter such that $G'/G''$ is greater than or equal to about 1, such as about 1.5 or about 2. The tooth whitening compositions disclosed herein ensure that the solid ingredients stay homogenously suspended in the hydrophobic fluid base, yielding a shelf-stable composition that is acceptable to consumers.

In various embodiments disclosed herein, the hydrophobic polymer carrier is a silicone pressure sensitive adhesive, such as a polydiorganosiloxane. The hydrophobic polymer carrier may be present in the tooth whitening composition in an amount ranging from about 20% to about 80%, for example, by weight relative to the total weight of the composition.

In embodiments disclosed herein, the at least one whitening agent may be hydrogen peroxide, and in certain exemplary embodiments, the hydrogen peroxide may be present in the tooth whitening composition in an amount ranging from about 0.1% to about 10% by weight, relative to the total weight of the composition.

According to certain embodiments disclosed herein, the tooth whitening composition may be anhydrous, and in certain embodiments the tooth whitening composition may be substantially free of polyethylene, for example substantially free of plastigel (a blend of mineral oil and polyethylene).

In certain embodiments disclosed herein, the fumed silica may be present in the tooth whitening composition in an amount ranging from about 1.5% to about 3%, by weight relative to the total weight of the composition. Likewise, in certain embodiments the sorbitan sebacate behenate polymer may be present in the tooth whitening composition in an amount ranging from about 1.5% to about 3%, by weight relative to the total weight of the composition. In various exemplary embodiments, the tooth whitening compositions disclosed herein may further comprise additional ingredients such as mineral oil, polyvinylpyrrolidone, flavoring agents, sweeteners, desensitizing agents, anti-microbial agents, anti-caries agents, anti-calculus agents, anti-inflammatory agents, vitamins, pigments and coloring agents, and preservatives.

Embodiments disclosed herein also include methods for whitening a surface of a tooth comprising contacting the surface of the tooth with a tooth whitening composition for a duration of time sufficient to effect whitening of the surface of the tooth, wherein the tooth whitening composition comprises at least one hydrophobic polymer carrier, fumed silica, sorbitan sebacate behenate polymer, and at least one whitening agent, and wherein the tooth whitening composition has a structural parameter such that $G'/G''$ is greater than or equal to about 1. In certain embodiments, the duration of time ranges from about 1 minute to about 45 minutes.

Embodiments disclosed herein also include methods for making a tooth whitening composition comprising combining at least one hydrophobic polymer carrier, fumed silica, sorbitan sebacate behenate polymer, and at least one whitening agent; and mixing the at least one hydrophobic polymer carrier, fumed silica, sorbitan sebacate behenate polymer, and at least one whitening agent to form a homogenous dispersion, wherein the tooth whitening composition has a structural parameter such that G'/G" is greater than or equal to about 1. According to certain embodiments, the method of making a tooth whitening composition may further comprise mixing at least one of flavoring agents, sweeteners, desensitizing agents, anti-microbial agents, anti-caries agents, anti-calculus agents, anti-inflammatory agents, vitamins, pigments and coloring agents, and preservatives.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
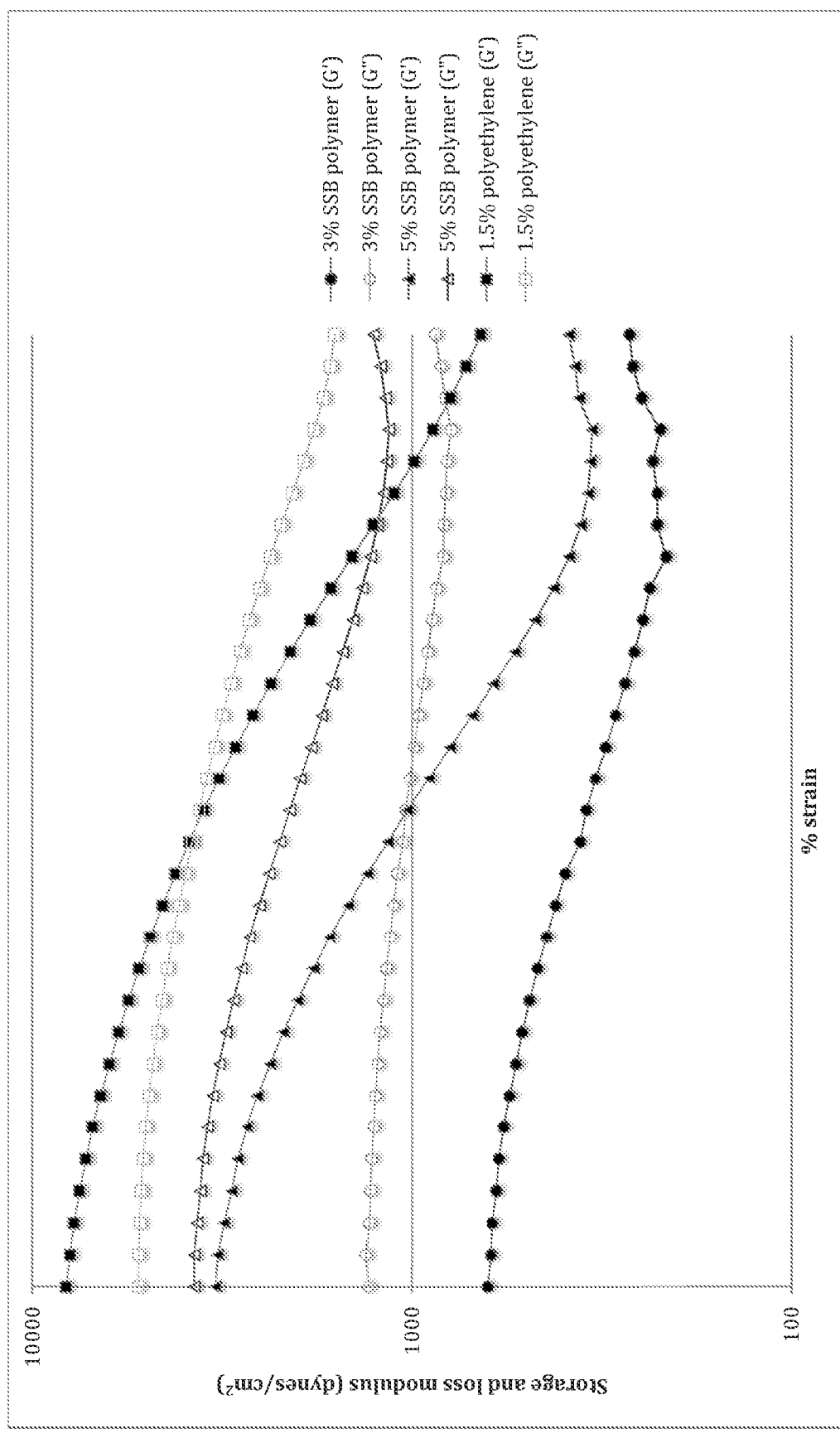
FIG. 1 is a graph plotting the strain sweep of G' and G" for sample compositions comprising 1.5% polyethylene, 3% sorbitan sebacate behenate polymer, and 5% sorbitan sebacate behenate polymer.

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, the term "one or more of" with respect to a listing of items such as, for example, A and B, means A alone, B alone, or A and B. The term "at least one of" is used to mean one or more of the listed items can be selected.

Unless otherwise specified, all percentages and amounts expressed herein and elsewhere in the specification should be understood to refer to percentages by weight. The amounts given are based on the active weight of the material.

Disclosed herein are tooth whitening compositions comprising at least one hydrophobic polymer carrier, such as at least one silicone adhesive; fumed silica; sorbitan sebacate behenate polymer; and at least one whitening agent, wherein the tooth whitening composition has a structural parameter such that G'/G" is greater than or equal to about 1, such as about 1.5 or about 2. In certain embodiments, the hydrophobic polymer carrier for adhering the tooth whitening composition to the tooth surface may be, for example, a silicone pressure sensitive adhesive.

The tooth whitening compositions disclosed herein may further comprise other additional ingredients that include those known to one of skill in the art, including one or more of the following components: fluoride ion sources, surfactants, flavoring agents, sweeteners, desensitizing agents, antimicrobial agents, anti-caries agents, anti-calculus agents, tartar control agents, anti-inflammatory agents, vitamins, pigments and coloring agents, preservatives, and enzymes, as will be discussed in greater detail below.

In some embodiments, the tooth whitening compositions disclosed herein are viscous liquids, such as gels, which maintain their consistency during storage, thereby enabling the product to be applied to the tooth surface, such as with a soft applicator pen or brush.

The viscosity of the tooth whitening composition disclosed herein may be greater than about 1,000 centipoise (cPs) and less than about 900,000 cPs, such as ranging from about 10,000 cPs to about 100,000 cPs; from about 50,000 to about 900,000 cPs, or ranging from about 200,000 cPs to about 600,000 cPs.

In certain embodiments, the tooth whitening compositions disclosed herein may be in the form of a viscoelastic fluid. As used herein, the term "viscoelastic fluid" refers to a complex fluid that exhibits mechanical properties that are both elastic solid-like, e.g., rubber) and viscous (liquid-like or flowable, e.g., water). A viscoelastic fluid composition may deform and flow under the influence of an applied shear stress (e.g. shaking or swishing in the mouth), but when the stress is removed, the composition will recover from the deformation. The elastic portion of the viscoelastic behavior may be quantified by the elastic modulus (G'), while the viscous portion may be quantified by the viscous modulus (G").

As used herein, "structured fluid" and "structured composition" may be used interchangeably, and refer to a fluid that exhibits a G' value greater than or equal to the G" value (i.e., the ratio of G' to G" is ≥ about 1) within the linear viscoelastic region of a strain sweep measurement, discussed below.

In some embodiments, fluid compositions are provided that comprise at least one structuring agent that forms a viscoelastic network with specific rheological characteristics.

As used herein, the term "structuring agent" refers to a substance that is able to form by itself, or in combination with another substance or substances, a structured network that provides a G'/G"≥ about 1. In certain embodiments, the structuring agents may comprise a combination of fumed silica and sorbitan sebacate behenate polymer. In certain exemplary embodiments, the tooth whitening composition is free of polyethylene as a structuring agent.

Various tests may be used to obtain the rheology profile of viscoelastic fluid compositions. One such test is a strain sweep test. The strain sweep test indicates whether a composition is structured or not. A strain sweep test measures G' and G", respectively. Taking the ratio of the G' value to the G" value within a linear viscoelastic region gives what is known as the "Structural Parameter." in some embodiments, the tooth whitening compositions disclosed herein have a G' to G" ratio of greater than or equal to about 1, such as greater than or equal to about 1.5, greater than or equal to about 1.75, or greater than or equal to about 2.0.

In a strain sweep test, the amplitude of the applied strain varies in the range 0.1%<y<100% while the frequency of oscillations is kept constant. The viscoelastic response of the material to the applied oscillatory strain is measured in terms of G' and G", the viscous and loss moduli, and valuable information may be obtained this way. In general, G' represents energy storage within the viscoelastic structure, and G" represents dissipation of this energy through flow. The linear viscoelastic region (LVR) is determined by the region of the strain sweep in which G' and G" remain constant with respect to the applied strain, and the ratio of elastic to viscous contribution (G'/G") can be calculated based on the G' and G" values within the LVR. This ratio provides a good indication of how structured a composition is, with a higher G'/G" ratio indicating that a more robust structure is present within the system. The yield stress value may also be determined from a strain sweep experiment, by plotting the elastic stress (G'×Strain) vs. Strain. With this information at hand, one can determine whether a certain viscoelastic material exhibits more solid-like or more fluid-like properties, and in this particular case the data can be utilized effectively to determine whether various aesthetics and solid materials can be successfully suspended within the composition.

In some embodiments, the tooth whitening composition disclosed herein is substantially anhydrous, meaning that no water is added. The tooth whitening composition may comprise trace levels of water from ingredients or from product manufacture; however, such trace levels are insubstantial and do not interfere with the hydrophobic character of the tooth whitening composition.

Hydrophobic Polymer Component

The tooth whitening compositions disclosed herein may comprise a carrier that comprises a hydrophobic polymer. The term "hydrophobic" or "water-insoluble" as applied to polymers and as employed herein refers to an organic polymer which is substantially non-aqueous having a water solubility of less than one gram per 100 grams of water at 25° C. In various embodiments, a hydrophobic polymer is compatible with the at least one whitening agent described herein. In certain embodiments, a hydrophobic polymer is selected for the carrier to produce a tooth whitening composition having a viscosity ranging from about 1,000 cPs to about 900,000 cPs, such as from about 10,000 cPs to about 900,000 cPs or from about 10,000 cPs to about 100,000 cPs.

One class of hydrophobic polymers that may be used according to certain exemplary embodiments comprise siloxane polymers, which are also generally known in the art as "silicone" polymers, such as silicone pressure sensitive adhesives (PSA). In certain embodiments disclosed herein, the hydrophobic polymers in the carrier are those in which a whitening agent can be dispersed and are well known in the art. Many such silicone polymers are commercially available. In various embodiments, a silicone-based hydrophobic polymer is a polyorganosiloxane, such as polydimethylsiloxane.

Exemplary polyorganosiloxanes may be produced by condensing a silicone resin and an organosiloxane, such as a polydiorganosiloxane. Such hydrophobic polymers are an elastomeric, tacky material, adhesion of which to dental enamel surfaces can be varied by altering the ratio of silicone resin to polydiorganosiloxane in the copolymer molecule. In certain embodiments, the polymers are pressure sensitive hydrophobic polymers specifically designed for pharmaceutical use and are permeable to many drug compounds and find application for the transdermal application of various compounds. In one such embodiment, the silicone polymers are the copolymer product of mixing a silanol terminated polydiorganosiloxane, such as polydimethyl siloxane, with a silanol-containing silicone resin whereby the silanol groups of the polydiorganosiloxane undergo a condensation reaction with the silanol groups of the silicone resin so that the polydiorganosiloxane is lightly crosslinked by the silicone resin (that is, the polydiorganosiloxane chains are bonded together through the resin molecules to give chain branching and entanglement and/or a small amount of network character) to form the silicone hydrophobic polymers. A catalyst, for example, an alkaline material, such as ammonia, ammonium hydroxide or ammonium carbonate, can be mixed with the silanol-terminated polydiorganosiloxane and the silicone resin to promote this crosslinking reaction. By copolymerizing the silicone resin with the silanol terminated polydiorganosiloxane, there results a polymer with self-adhering properties and the cohesive properties of a soft elastomer matrix characteristic of pressure sensitive polymers being distinguished from the hard, non-elastomeric properties of other silicone resins. In one embodiment, hydrophobic polymers used in the carrier are available from the Dow-Corning Company under the brand name BIO-PSA.

The modification of a ratio of silicone resin to polydiorganosiloxane modifies the tackiness of the hydrophilic polymer. This ratio may, for example, be in the range of 70:30 to 50:50. For example, the BIO-PSA silicone sold by Dow-Corning is available in three silicone resin to silicone polymer ratios: namely, 65/35 (low tack), 60/40 (medium tack), and 55/45 (high tack), as modifying the silicone resin to polydiorganosiloxane ratio of the PSA will modify the tackiness of the PSA. Such a polyorganosiloxane pressure sensitive adhesive is available dissolved in either ethyl acetate solvent or dimethicone. An exemplary suitable silicone PSA is Silicone Adhesive 8-7016, commercially available from Dow Corning.

In some embodiments, the siloxane polymers that can function as part of the hydrophobic component are in the form of a fluid. Polysiloxane fluids useful herein for the hydrophobic silicone material component include those with a viscosity, at 25° C., of about 1 milliPascal-sec (mPa-s) to about 1000 mPa-s, or about 2 mPa-s to about 500 mPa-s, or about 20 mPa-s to about 400 mPa-s. Polysiloxane fluids for use herein can be linear or cyclic, and can be substituted with a wide variety of substituents. In certain embodiments, substituents include methyl, ethyl and phenyl substituents. Suitable polysiloxane fluids include linear polysiloxane polymers such as dimethicone and other low viscosity analogues of the polysiloxane materials, in certain embodiments having a viscosity, at 25° C., of 200 mPa-s or less and cyclomethicone, and other cyclic siloxanes having for example a viscosity, at 25° C., of 200 mPa-s or less. Other fluids include polysiloxane polyether copolymers and hydroxy terminated polydimethyl-siloxane fluid (e.g., Dow Corning ST-DIMETHICONOL™ 40, Dow Corning SGM 36, SGM3). Commercial examples of materials that are suitable for use herein include the DC200 series fluids marketed by Dow-Corning Corporation and the AK Fluid series marketed by Wacker-Chemie GmbH, Munchen, Germany. High molecular silicone resins with a polysiloxane blend may also be used including powdered trimethylsiloxysilicate, for example, Dow Corning 593 fluid, Wacker Belsil TMS 803. Another suitable silicone fluid from Dow Corning is Q7-9210.

While not intending on being bound by any theory of operability, it is believed that hydrophobic adhesives (such as silicone resin, silicone adhesives, etc.) which are substantive to, and can be readily adhered to, the tooth surface, surprisingly can be combined with a peroxide, such as hydrogen peroxide, and adhesion enhancing agents that act as structuring agents, including fumed silica and sorbitan sebacate behenate polymer, to form a stable, highly retentive and efficacious tooth whitening gel. This was despite the expectation that the combination of fumed silica and sorbitan sebacate behenate polymer would not yield a stable composition with an adequate viscoelastic structure for maintaining the solids homogenously dispersed in the tooth whitening composition.

In certain embodiments disclosed herein, the hydrophobic polymer carrier, such as the polydiorganosiloxane, may comprises from about 20% to about 80% by weight of the tooth whitening composition, such as, for example about 40% to about 80%, from about 60% to about 80%, from about 70% to about 80%, or about 75%.

Adhesion Enhancing Agents

In various embodiments, the tooth whitening compositions disclosed herein comprise at least two adhesion enhancing agents that act as structuring agents in the compositions and augment adhesion of the whitening composition to the surface of the tooth, i.e., adhesion to the enamel. In embodiments disclosed herein, the at least two adhesion enhancing agents comprise a combination of fumed silica and sorbitan sebacate behenate polymer. The combination of the fumed silica and sorbitan sebacate behenate polymer act as structuring agents, creating a viscoelastic structure together with the hydrophobic polymer carrier, such that G'/G" is greater than or equal to 1, This viscoelastic structure ensures that the solid ingredients remain homogenously suspended in the tooth whitening composition, such that the composition remains stable and has an adequate shelf life after formulation.

Fumed silica, also known as pyrogenic silica, is an inorganic material comprising amorphous silica. The individual silica particles may agglomerate into a three-dimensional structure having a low bulk density and high surface area. Exemplary filmed silicas may include CAB-O-SIL fumed silica manufactured by Cabot Corporation and AEROSIL fumed silica manufactured by Evonik industries. In certain embodiments disclosed herein, the fumed silica may be present in the tooth whitening composition in an amount ranging from about 1% to about 5%, such as about 1.5% to about 3%, by weight relative to the total weight of the composition.

Sorbitan sebacate behenate polymer is also known as sorbitol sebacic acid copolymer behenate, and is copolymer of sorbitol and sebacic acid esterified with behenic acid. It is known for use in controlling viscosity. In certain embodiments disclosed herein, the sorbitan sebacate behenate polymer may be present in the tooth whitening composition in an amount ranging from about 1% to about 5%, such as about 1.5% to about 3%, by weight relative to the total weight of the composition.

Additional adhesion enhancing agents may be used in accordance with various embodiments of the tooth whitening composition disclosed herein. Exemplary adhesion enhancing agents disclosed herein include inorganic materials as well as organic natural and synthetic polymers. In certain exemplary embodiments, the inorganic adhesion enhancing material, such as silica, may be surface treated to compatibilize the adhesion enhancing agent with the hydrophobic components in the tooth whitening composition.

Organic materials which may be included in the tooth whitening compositions disclosed herein to enhance the properties of the hydrophobic polymers may include adhesion enhancing agents such as waxes, inclusive of beeswax, mineral oil, plastigel (a blend of mineral oil and polyethylene), petrolatum, white petrolatum, shellac, versagel (blend of liquid paraffin, butene/ethylene/styrene hydrogenated copolymer), polyethylene waxes, microcrystalline waxes, polyisobutene, polyvinylpyrrolidone/vinyl acetate copolymers, and insoluble polyacrylate copolymers.

The tooth whitening compositions disclosed herein may further comprise crospovulone (poly[N-vinyl-2-pyrrolidone]) as an adhesion enhancing agent. Crospovidone may be present in the composition in an amount ranging from about 10% to about 30%, by weight relative to the total weight of the tooth whitening composition, such as ranging from about 15% to about 25%, or ranging from about 18% to about 25%.

Also effective as adhesion enhancing agents are liquid hydrophilic polymers including polyethylene glycols, nonionic polymers of ethylene oxide having the general formula: $HOCH_2(CH_2OCH_2)_nCH_2OH$, wherein n represents the average number of oxyethylene groups. Polyethylene glycols available from Dow Chemical are designated by a number such as 200, 300, 400, 600, and 2000, which represents the approximate average molecular weight of the polymer, as well as nonionic block copolymer of ethylene oxide and propylene oxide of the formulas: $HO(CH_4O)_a(C_3H_6O)_b(C_2H_4O)_cH$.

The block copolymer may be chosen (with respect to a, b and c) such that the ethylene oxide constituent comprises from about 65% to about 75% by weight, of the copolymer molecule and the copolymer has an average molecular weight of from about 2,000 to about 15,000 with the copolymer being present in the tooth whitening composition in such concentration that the composition is a gel at room temperature (about 23° C.).

One block copolymer for use herein is available commercially from BASF and designated PLURAFLO L1220, which has an average molecular weight of 9,800. The hydrophilic poly (ethylene oxide) block averages 65% by weight of the polymer.

At least one additional adhesion enhancing agent in addition to the fumed silica and sorbitan sebacate behenate polymer that may be employed in compositions of various embodiments disclosed herein may present in an amount ranging from 1% to 80% by weight, relative to the total weight of the tooth whitening composition, such as, for example, ranging from about 1.5% to 75% by weight.

Whitening Agents

In various embodiments, the tooth whitening compositions disclosed herein comprise at least one whitening agent as a main active ingredient. In certain embodiments, the at least one whitening agent is a peroxide compound. As further discussed below, a "whitening agent" is a material which effects whitening of a tooth surface to which it is applied.

As referred to herein, a "peroxide compound" is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxy phthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof.

Peroxide releasing compounds that may be mentioned for use in the tooth whitening compositions disclosed herein include peroxide containing compounds such as urea peroxide, sodium percarbonate, sodium perborate and polyvinylpyrrolidone-$H_2O_2$ complexes (hereinafter "PVP-$H_2O_2$"). Polyvinylpyrrolidone is also known as poly-N-vinyl-poly-2-pyrrolidone and commonly abbreviated to "PVP". PVP generally refers to a polymer containing vinylpyrrolidone (also referred to as N-vinylpyrrolidone, N-vinyl-2-pyrrolidione and N-vinyl-2-pyrrolidinone) as a monomeric unit. The monomeric unit consists of a polar imide group, four non-polar methylene groups and a non-polar methane group.

Both linear and cross-linked complexes of PVP-$H_2O_2$ are known in the art, and PVP-$H_2O_2$ is considered to be stable in an anhydrous environment. Upon exposure to highly aqueous environments, such as in the oral cavity, the PVP-$H_2O_2$ dissociates into individual species (PVP polymer and $H_2O_2$). In one embodiment, the PVP-$H_2O_2$ complex is 80% by weight polyvinylpyrrolidone and 20% by weight $H_2O_2$.

In alternate embodiments disclosed herein, the at least one whitening agent comprises a liquid peroxide solution. The hydrophobic polymer carrier of the whitening composition provides sufficient stability to permit the use of a liquid hydrogen peroxide. The liquid hydrogen peroxide comprises $H_2O_2$ generally contained in an aqueous water-based solution. In some embodiments, the liquid hydrogen peroxide has a concentration of peroxide to the total solution ranging from about 0.035% to about 17.5%, such as from about 3% to about 10% by weight, which for example may be achieved by adding a 35 wt % aqueous $H_2O_2$ solution at a concentration of from about 0.1 wt % to about 50 wt %, such as about 8 wt % to about 29 wt %, or from about 15 wt % to about 25 wt %. Additionally, at least one stabilizer may be present. For example, a 3% hydrogen peroxide solution with about 0.1% to about 0.5% of at least one stabilizer may be used. Acetanilide or a similar organic material can also be used with a pyrophosphate stabilizer such as sodium acid pyrophosphate, present in an amount ranging from about 0.1% to about 1.0%, such as about 0.5%.

In certain embodiments, the tooth whitening composition may further comprise at least one agent to enhance release of the peroxide in the oral cavity as a part of the peroxide component whitening agent. POLY-PORE, which is an allyl methacrylate crosspolymer, available from Amcol health & Beauty Solutions, Inc., is an exemplary enhancing agent.

In various embodiments, the at least one whitening agent is present in the tooth whitening composition in an amount ranging from about 0.035% to 17.5%, such as from about 0.1% to about 10%, or from about 0.1% to about 6%, by weight relative to the total weight of the tooth whitening composition.

Additional Components

As previously described, many other components may further be included in the whitening compositions of the present invention, and include surfactants, flavoring agents, sweetening agents, desensitizing agents, anti-microbial agents, anti-caries agents, anti-calculus agents, anti-inflammatory agents, vitamins, pigments and coloring agents, enzymes, preservatives, and tartar control agents, for example.

In certain embodiments disclosed herein, the tooth whitening composition may further comprise at least one flavoring agent. The at least one flavoring agent, may, for example, be selected from essential oils, as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent may be incorporated in the tooth whitening compositions disclosed herein at a concentration ranging from 0.01% to about 2% by weight, such as about 0.1% to about 0.6% by weight.

In embodiments where the tooth whitening composition is sweetened, at least one sweetening agent may be used as an alternative or as a complement to the at least one flavoring agent. Suitable sweetening agents may be water-soluble and include, for example, sodium saccharin, sodium cyclamate, xylitol, perillartien, D-tryptophan, aspartame, dihydrochalcones and the like. The at least one sweetening agent may be present in the tooth whitening composition in an amount ranging from about 0.01% to about 1% by weight, such as about 0.3%.

Exemplary antimicrobial agents may include those typically used in oral care compositions, such as Triclosan, chlorhexidine, copper-, zinc-and stannous salts such as zinc citrate, zinc sulfate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2'methylenebis-(4-chloro-6-bromophenol).

Exemplary anti-inflammatory agents may include those typically used in oral care compositions, such as ibuprofen, flurbiprofen, aspirin, indomethacine. Exemplary anti-caries agents may include ingredients such as sodium-, calcium-, magnesium-and stannous fluoride, aminefluorides, disodium monofluorophosphate and sodium trimetaphosphate. Exemplary vitamins may include ingredients such as Vitamin C. Exemplary desensitizing agents may include ingredients such as potassium citrate, potassium chloride, potassium tartrate, potassium bicarbonate, potassium oxalate, potassium nitrate and strontium salts. Exemplary anti-calculus agents may include ingredients such as pyrophosphate salts including the mono, di, tri and tetra alkali metal and ammonium pyrophosphate and tripolyphosphate salts. Exemplary enzymes may include papain and glucoamylase.

Some embodiments provide compositions wherein at least one of ingredients is a fluoride ion source selected from stannous fluoride, sodium fluoride, potassium fluoride, sodium monofluorophosphate, sodium fluorosilicate, ammonium fluorosilicate, amine fluoride, and ammonium fluoride.

Also disclosed herein are methods for whitening a surface of a tooth in an oral cavity of a human or other animal subject which comprises (a) applying a tooth whitening composition as disclosed herein to the tooth surface to be whitened for a plurality of minutes per day; and (b) repeating step (a) for multiple days to thereby whiten the teeth. Also disclosed herein is a method for whitening a surface of a tooth comprising applying to the surface of the tooth a composition comprising at least one hydrophobic polymer carrier, fumed silica, sorbitan sebacate behenate polymer, and at least one whitening agent.

Exemplary methods disclosed herein comprise contacting the tooth whitening composition with the surface of the tooth. The contacting may occur for a duration of time sufficient to satisfactorily effect whitening of the teeth. Thus, the contacting occurs for a sufficient period of time to at least partially whiten teeth. This can be a period of time ranging from about 1 minute to about 2 hours or longer. In certain embodiments, the contacting is for a period of time ranging from about 1 minute to about 5 minutes, from about 1 minute to about 45 minutes, from about 5 minutes to about 45 minutes, or from about 5 minutes to about 30 minutes.

In certain embodiments disclosed herein, a substantially non-aqueous tooth whitening composition may be effective over a longer period of time, since it is not significantly diluted or washed away in the oral cavity during the treatment time. The tooth whitening composition can be removed as and when required, at will, by an employment of standard oral hygiene procedures such as brushing or by rinsing with an alcoholic mouthwash. While in place, the composition may release agents contained therein at a slow, relatively constant rate and in concentration sufficient to effect stain removal from the teeth.

Further disclosed herein are methods of making a tooth whitening composition as disclosed herein. The tooth whitening compositions disclosed herein may, in certain embodiments, be prepared by adding and mixing the ingredients of the composition in a suitable vessel, such as a stainless steel tank provided with a mixer. In the preparation of the tooth whitening composition, the ingredients may be added to the mixer in the following order: hydrophobic polymer component, such as the silicone based pressure sensitive polymer; peroxide whitening agent; adhesion enhancing agents, including fumed silica and sorbitan sebacate behenate polymer; and any desired flavoring or sweetener. The ingredients may then be mixed to form a homogenous dispersion/solution.

The tooth whitening composition disclosed herein may be prepared in the form of a flowable viscous liquid dispersion, such as a gel, comprising at least one whitening agent and is applied as such to the user's teeth as by painting the teeth with a soft applicator brush. Application by the user leaves a coating of the composition on the teeth. Contact with saliva causes the slow release of $H_2O_2$ from the hydrophobic material matrix to the applied tooth site from the composition, providing prolonged whitening treatment of the tooth sites.

EXAMPLES

Comparative Example 1

Fumed silica and sorbitan sebacate behenate polymer were evaluated individually as potential rheology modifiers/structuring agents that may be utilized as a replacement for polyethylene in a tooth whitening composition. Although both fumed silica and sorbitan sebacate behenate polymer individually provided thickening as a result of increased viscosity, neither material provided the preferred viscoelastic structure. The preferred viscoelastic structure can be described as a structural parameter (G'/G") equal to or greater than 1. Three formulations were prepared as disclosed below in Table 1.

TABLE 1

| Ingredient | Sample with sorbitan sebacate behenate polymer | Sample with fumed silica | Sample with polyethylene |
| --- | --- | --- | --- |
| Trimethylsiloxy-silicate/dimethiconol crosspolymer | 12.0% | 12.0% | 12.0% |
| Dimethicone | QS | QS | QS |
| PVP | 18.0%-25.0% | 18.0%-25.0% | 18.0%-25.0% |
| Hydrogen peroxide | 0.1%-6.0% | 0.1%-6.0% | 0.1%-6.0% |
| Sodium saccharin | 0.3% | 0.3% | 0.3% |
| Sorbitan sebacate behenate polymer | 3.0%-5.0% | — | — |
| Fumed silica | — | 3.0%-5.0% | — |
| Polyethylene | — | — | 1.5%-2.0% |
| Mineral oil | 25.0%-35.0% | 0-35% | 25.0%-35.0% |
| Flavor | 0.6% | 0.6% | 0.6% |
| Total | 100.0% | 100.0% | 100.0% |

A strain sweep experiment was then performed on a 3% sorbitan sebacate behenate polymer sample, a 5% sorbitan sebacate behenate polymer sample, and a 1.5% polyethylene control sample. The experiment was performed at 25° C. FIG. 1 is a graph illustrating the results of the strain sweep experiment, and Table 2 below lists the viscoelastic G' and G" values for the 3% sorbitan sebacate behenate polymer sample, 5% sorbitan sebacate behenate polymer sample, and 1.5% polyethylene control at various strain percentages.

TABLE 2

| Strain (%) | 3% SSB Polymer | | | 5% SSB Polymer | | | 1.5% Polyethylene | | |
| --- | --- | --- | --- | --- | --- | --- | --- | --- | --- |
| | G' | G" | G'/G" | G' | G" | G'/G" | G' | G" | G'/G" |
| 0.10 | 630.48 | 1301.44 | 0.48 | 3295.93 | 3752.64 | 0.88 | 8141.14 | 5269.11 | 1.55 |
| 0.13 | 618.56 | 1320.36 | 0.47 | 3254.46 | 3755.02 | 0.87 | 7949.57 | 5262.37 | 1.51 |
| 0.16 | 614.48 | 1294.65 | 0.47 | 3129.04 | 3685.78 | 0.85 | 7769.24 | 5222.52 | 1.49 |
| 0.20 | 598.85 | 1285.03 | 0.47 | 2989.74 | 3614.90 | 0.83 | 7506.13 | 5182.88 | 1.45 |
| 0.25 | 589.74 | 1277.02 | 0.46 | 2880.10 | 3559.09 | 0.81 | 7222.17 | 5110.23 | 1.41 |
| 0.31 | 572.81 | 1260.59 | 0.45 | 2719.22 | 3461.30 | 0.79 | 6935.88 | 5035.59 | 1.38 |
| 0.40 | 552.24 | 1249.34 | 0.44 | 2552.35 | 3358.97 | 0.76 | 6618.90 | 4937.44 | 1.34 |
| 0.50 | 530.59 | 1232.55 | 0.43 | 2367.73 | 3229.64 | 0.73 | 6284.38 | 4826.65 | 1.30 |
| 0.63 | 511.90 | 1215.01 | 0.42 | 2184.14 | 3095.81 | 0.71 | 5942.41 | 4700.55 | 1.26 |

TABLE 2-continued

| Strain | 3% SSB Polymer | | | 5% SSB Polymer | | | 1.5% Polyethylene | | |
|---|---|---|---|---|---|---|---|---|---|
| (%) | G' | G" | G'/G" | G' | G" | G'/G" | G' | G" | G'/G" |
| 0.79 | 489.76 | 1190.79 | 0.41 | 1999.76 | 2958.45 | 0.68 | 5592.05 | 4565.39 | 1.22 |
| 1.00 | 466.63 | 1167.38 | 0.40 | 1821.12 | 2817.45 | 0.65 | 5245.27 | 4422.57 | 1.19 |
| 1.25 | 441.68 | 1143.33 | 0.39 | 1647.46 | 2674.75 | 0.62 | 4898.96 | 4274.30 | 1.15 |
| 1.58 | 418.18 | 1118.93 | 0.37 | 1473.76 | 2527.16 | 0.58 | 4547.48 | 4115.86 | 1.10 |
| 1.99 | 394.19 | 1093.65 | 0.36 | 1312.36 | 2380.68 | 0.55 | 4203.40 | 3955.20 | 1.06 |
| 2.50 | 359.81 | 1056.43 | 0.34 | 1157.84 | 2231.60 | 0.52 | 3870.93 | 3801.17 | 1.02 |
| 3.15 | 346.93 | 1037.75 | 0.33 | 1028.56 | 2101.97 | 0.49 | 3543.47 | 3641.46 | 0.97 |
| 3.96 | 327.75 | 1012.74 | 0.32 | 902.09 | 1968.21 | 0.46 | 3229.86 | 3482.88 | 0.93 |
| 4.99 | 308.72 | 986.59 | 0.31 | 792.77 | 1844.52 | 0.43 | 2921.97 | 3317.46 | 0.88 |
| 6.28 | 290.80 | 960.31 | 0.30 | 694.93 | 1729.11 | 0.40 | 2633.65 | 3164.85 | 0.83 |
| 7.91 | 274.05 | 933.92 | 0.29 | 609.14 | 1622.15 | 0.38 | 2357.33 | 3003.88 | 0.78 |
| 9.96 | 259.07 | 908.48 | 0.29 | 534.85 | 1522.93 | 0.35 | 2096.82 | 2842.24 | 0.74 |
| 12.53 | 246.28 | 884.25 | 0.28 | 473.34 | 1433.06 | 0.33 | 1855.43 | 2680.33 | 0.69 |
| 15.78 | 236.11 | 861.93 | 0.27 | 423.53 | 1353.97 | 0.31 | 1635.64 | 2519.77 | 0.65 |
| 19.86 | 213.48 | 826.47 | 0.26 | 385.35 | 1285.93 | 0.30 | 1438.62 | 2362.61 | 0.61 |
| 25.01 | 225.84 | 824.51 | 0.27 | 358.86 | 1230.67 | 0.29 | 1265.03 | 2210.33 | 0.57 |
| 31.48 | 225.38 | 814.00 | 0.28 | 343.33 | 1189.38 | 0.29 | 1114.98 | 2065.09 | 0.54 |
| 39.64 | 231.39 | 808.97 | 0.29 | 338.49 | 1164.55 | 0.29 | 986.44 | 1930.10 | 0.51 |
| 49.90 | 221.51 | 787.10 | 0.28 | 335.32 | 1150.55 | 0.29 | 879.63 | 1810.42 | 0.49 |
| 62.82 | 247.91 | 815.56 | 0.30 | 362.89 | 1175.24 | 0.31 | 791.96 | 1711.83 | 0.46 |
| 79.08 | 261.30 | 840.00 | 0.31 | 371.69 | 1208.51 | 0.31 | 719.82 | 1640.26 | 0.44 |
| 99.57 | 266.82 | 868.95 | 0.31 | 385.66 | 1264.11 | 0.31 | 658.18 | 1596.62 | 0.41 |

As shown in Table 2, none of the strain percentages for either the 3% sorbitan sebacate behenate polymer sample or the 5% sorbitan sebacate behenate polymer sample yielded a structural parameter (G'/G") of greater than or equal to 1. Based on this, it can be inferred that the solid powder ingredients will not stay homogenously suspended in the hydrophobic matrix, and therefore both the 3% and 5% sorbitan sebacate behenate polymer formulations will lack sufficient shelf stability.

Figure 2:
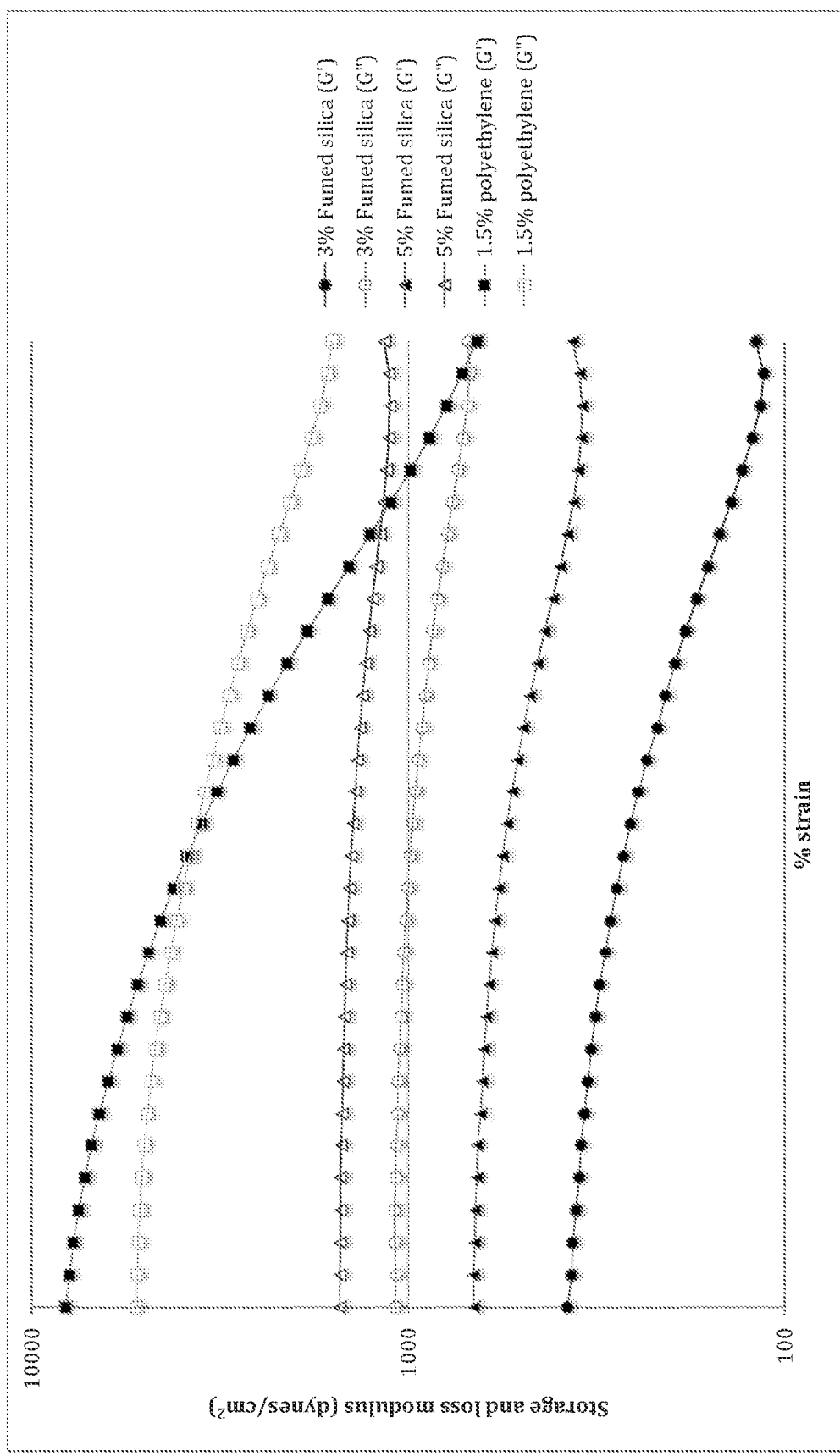
FIG. 2 is a graph plotting the strain sweep of G' and G" for sample compositions comprising 1.5% polyethylene, 3% fumed silica, and 5% fumed silica.

Similarly, a strain sweep experiment was also performed on a 3% fumed silica sample, a 5% fumed silica sample, and a 1.5% polyethylene control sample. The experiment was performed at 25° C. FIG. 2 is a graph illustrating the results of the strain sweep experiment, and Table 3 below lists the viscoelastic G' and G" values for the 3% fumed silica sample, 5% fumed silica sample, and 1.5% polyethylene control at various strain percentages.

TABLE 3

| Strain | 3% Fumed silica | | | 5% Fumed silica | | | 1.5% Polyethylene | | |
|---|---|---|---|---|---|---|---|---|---|
| (%) | G' | G" | G'/G" | G' | G" | G'/G" | G' | G" | G'/G" |
| 0.10 | 377.697 | 1081.29 | 0.35 | 668.65 | 1521.45 | 0.44 | 8141.14 | 5269.11 | 1.55 |
| 0.13 | 368.386 | 1077.36 | 0.34 | 670.391 | 1517.3 | 0.44 | 7949.57 | 5262.37 | 1.51 |
| 0.16 | 366.001 | 1084.96 | 0.34 | 665.001 | 1514.1 | 0.44 | 7769.24 | 5222.52 | 1.49 |
| 0.20 | 358.302 | 1087.96 | 0.33 | 664.766 | 1513.05 | 0.44 | 7506.13 | 5182.88 | 1.45 |
| 0.25 | 351.803 | 1078.04 | 0.33 | 656.625 | 1512.26 | 0.43 | 7222.17 | 5110.23 | 1.41 |
| 0.31 | 347.952 | 1076.43 | 0.32 | 655.018 | 1507.53 | 0.43 | 6935.88 | 5035.59 | 1.38 |
| 0.40 | 340.798 | 1067.06 | 0.32 | 642.074 | 1497.76 | 0.43 | 6618.90 | 4937.44 | 1.34 |
| 0.50 | 333.961 | 1065.24 | 0.31 | 635.042 | 1490.34 | 0.43 | 6284.38 | 4826.65 | 1.30 |
| 0.63 | 326.765 | 1053.94 | 0.31 | 628.554 | 1485.02 | 0.42 | 5942.41 | 4700.55 | 1.26 |
| 0.79 | 318.737 | 1044.94 | 0.31 | 619.721 | 1476.64 | 0.42 | 5592.05 | 4565.39 | 1.22 |
| 1.00 | 310.58 | 1036.42 | 0.30 | 610.089 | 1467.42 | 0.42 | 5245.27 | 4422.57 | 1.19 |
| 1.25 | 299.471 | 1028.4 | 0.29 | 599.586 | 1458.38 | 0.41 | 4898.96 | 4274.30 | 1.15 |
| 1.58 | 290.364 | 1015.35 | 0.29 | 588.077 | 1446.67 | 0.41 | 4547.48 | 4115.86 | 1.10 |
| 1.99 | 279.371 | 1003.47 | 0.28 | 575.606 | 1434.36 | 0.40 | 4203.40 | 3955.20 | 1.06 |
| 2.50 | 268.066 | 990.337 | 0.27 | 561.633 | 1419.98 | 0.40 | 3870.93 | 3801.17 | 1.02 |
| 3.15 | 256.617 | 975.866 | 0.26 | 546.459 | 1403.32 | 0.39 | 3543.47 | 3641.46 | 0.97 |
| 3.96 | 244.981 | 960.642 | 0.26 | 530.162 | 1385.58 | 0.38 | 3229.86 | 3482.88 | 0.93 |
| 4.99 | 232.886 | 943.899 | 0.25 | 512.528 | 1365.77 | 0.38 | 2921.97 | 3317.46 | 0.88 |
| 6.28 | 217.964 | 922.964 | 0.24 | 494.368 | 1345.66 | 0.37 | 2633.65 | 3164.85 | 0.83 |
| 7.91 | 207.467 | 905.138 | 0.23 | 475.061 | 1323.95 | 0.36 | 2357.33 | 3003.88 | 0.78 |
| 9.96 | 195.541 | 884.319 | 0.22 | 454.18 | 1298.16 | 0.35 | 2096.82 | 2842.24 | 0.74 |
| 12.53 | 183.461 | 861.445 | 0.21 | 433.806 | 1271.74 | 0.34 | 1855.43 | 2680.33 | 0.69 |
| 15.78 | 171.417 | 837.478 | 0.20 | 413.917 | 1244.46 | 0.33 | 1635.64 | 2519.77 | 0.65 |
| 19.86 | 159.894 | 812.776 | 0.20 | 394.952 | 1216.3 | 0.32 | 1438.62 | 2362.61 | 0.61 |
| 25.01 | 148.913 | 787.388 | 0.19 | 378.001 | 1188.83 | 0.32 | 1265.03 | 2210.33 | 0.57 |
| 31.48 | 138.737 | 762.16 | 0.18 | 363.955 | 1163.81 | 0.31 | 1114.98 | 2065.09 | 0.54 |
| 39.64 | 129.586 | 737.952 | 0.18 | 353.337 | 1142.28 | 0.31 | 986.44 | 1930.10 | 0.51 |
| 49.90 | 121.809 | 715.73 | 0.17 | 346.836 | 1126.27 | 0.31 | 879.63 | 1810.42 | 0.49 |
| 62.82 | 115.926 | 697.287 | 0.17 | 345.268 | 1119 | 0.31 | 791.96 | 1711.83 | 0.46 |
| 79.08 | 113.563 | 686.375 | 0.17 | 349.855 | 1125.13 | 0.31 | 719.82 | 1640.26 | 0.44 |
| 99.57 | 119.055 | 692.426 | 0.17 | 365.91 | 1157.21 | 0.32 | 658.18 | 1596.62 | 0.41 |

As shown in Table 3, none of the strain percentages for either the 3% fumed silica sample or the 5% fumed silica sample yielded a structural parameter (G'/G") of greater than or equal to 1. Based on this, it can be inferred that the solid powder ingredients will not stay homogenously suspended in the hydrophobic matrix, and therefore both the 3% and 5% fumed silica formulations will lack sufficient shelf stability.

Example 2

A formulation was prepared according to Table 4, below, comprising both fumed silica and sorbitan sebacate behenate polymer, but not containing polyethylene. The formulation was compared to a sample comprising polyethylene but not containing either fumed silica or sorbitan sebacate behenate polymer.

TABLE 4

| Ingredient | Sample with sorbitan sebacate behenate polymer and fumed silica | Sample with polyethylene |
| --- | --- | --- |
| Trimethylsiloxysilicate/ dimethiconol crosspolymer | 12.0% | 12.0% |

TABLE 4-continued

| Ingredient | Sample with sorbitan sebacate behenate polymer and fumed silica | Sample with polyethylene |
| --- | --- | --- |
| Dimethicone | QS | QS |
| PVP | 18.0%-25.0% | 18.0%-25.0% |
| Hydrogen peroxide | 0.1%-6.0% | 0.1%-6.0% |
| Sodium saccharin | 0.3% | 0.3% |
| Sorbitan sebacate behenate polymer | 1.5%-3.0% | — |
| Fumed silica | 1.5%-3.0% | — |
| Polyethylene | — | 1.5%-2.0% |
| Mineral oil | 25.0%-35.0% | 25.0%-35.0% |
| Flavor | 0.6% | 0.6% |
| Total | 100.0% | 100.0% |

Figure 3:
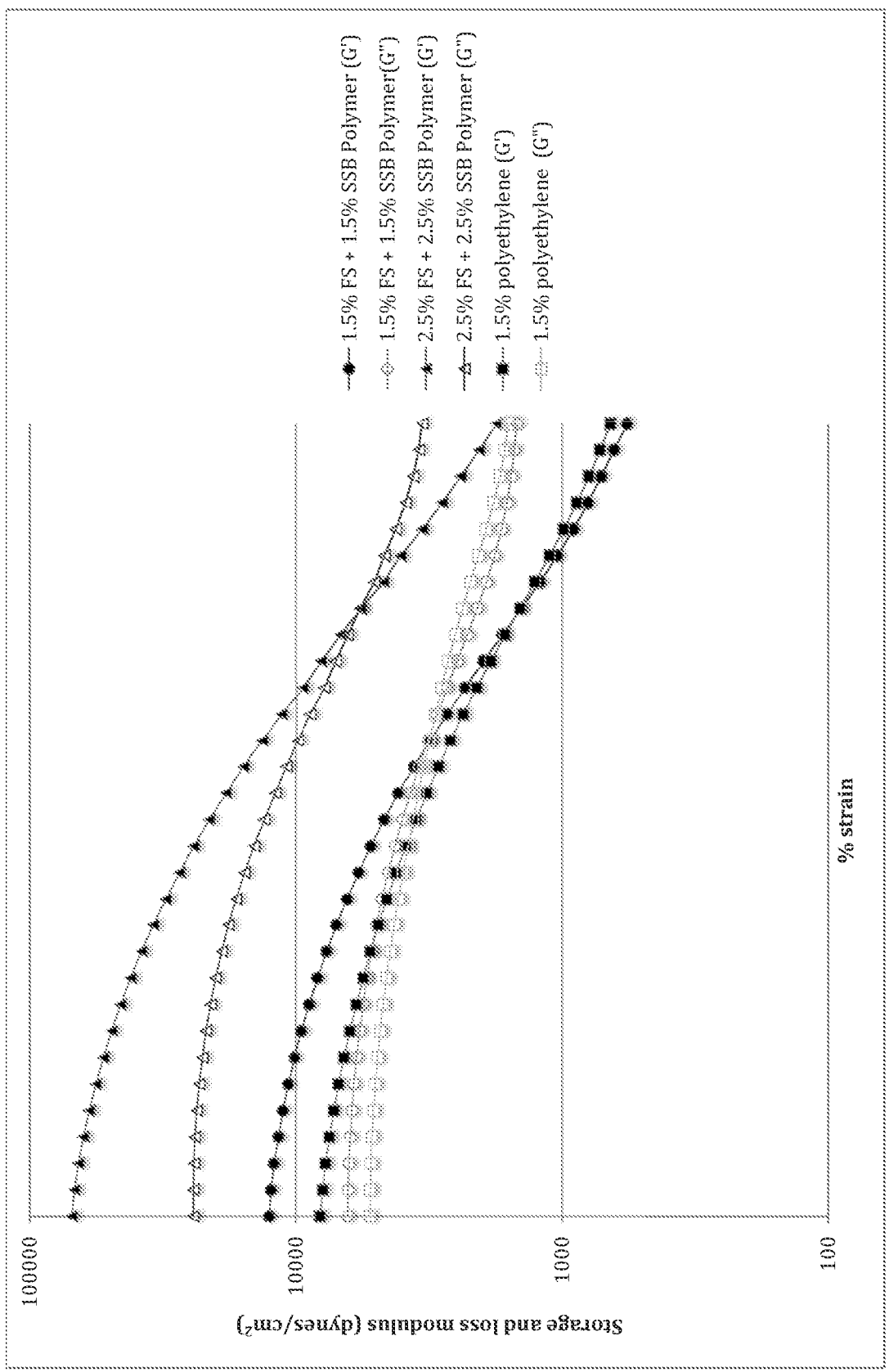
FIG. 3 is a graph plotting the strain sweep of G' and G" for sample compositions comprising 1.5% polyethylene; 2.5% fumed silica plus 2.5% sorbitan sebacate behenate polymer; and 1.5% fumed silica plus 1.5% sorbitan sebacate behenate polymer.

A strain sweep experiment was then performed on the following three samples: formulation comprising 1.5% fumed silica and 1.5% sorbitan sebacate behenate polymer; formulation comprising 2.5% fumed silica and 2.5% sorbitan sebacate behenate polymer; and formulation comprising 1.5% polyethylene. The experiment was performed at 25° C. FIG. 3 is a graph illustrating the results of the strain sweep experiment, and Table 5 below lists the viscoelastic G' and G" values for the above-listed three formulations at various strain percentages.

TABLE 5

| Strain (%) | 1.5% FS and 1.5% SSBP | | | 2.5% FS and 2.5% SSBP | | | 1.5% Polyethylene | | |
| --- | --- | --- | --- | --- | --- | --- | --- | --- | --- |
| | G' | G" | G'/G" | G' | G" | G'/G" | G' | G" | G'/G" |
| 0.10 | 12645.6 | 6398.41 | 1.98 | 69623.9 | 24283.8 | 2.87 | 8141.14 | 5269.11 | 1.55 |
| 0.13 | 12434.8 | 6387.3 | 1.95 | 68049.8 | 24290.2 | 2.80 | 7949.57 | 5262.37 | 1.51 |
| 0.16 | 12121.7 | 6342.92 | 1.91 | 65756.1 | 24186.2 | 2.72 | 7769.24 | 5222.52 | 1.49 |
| 0.20 | 11674.5 | 6267.45 | 1.86 | 63008.3 | 23978.2 | 2.63 | 7506.13 | 5182.88 | 1.45 |
| 0.25 | 11223.5 | 6180.9 | 1.82 | 59808.4 | 23598.7 | 2.53 | 7222.17 | 5110.23 | 1.41 |
| 0.31 | 10714.9 | 6076.35 | 1.76 | 56496.1 | 23098.4 | 2.45 | 6935.88 | 5035.59 | 1.38 |
| 0.40 | 10130.4 | 5935.59 | 1.71 | 52962.3 | 22464.6 | 2.36 | 6618.90 | 4937.44 | 1.34 |
| 0.50 | 9532.12 | 5773.62 | 1.65 | 49348.6 | 21791 | 2.26 | 6284.38 | 4826.65 | 1.30 |
| 0.63 | 8918.36 | 5599.85 | 1.59 | 45621.4 | 20952.2 | 2.18 | 5942.41 | 4700.55 | 1.26 |
| 0.79 | 8310.43 | 5413.93 | 1.54 | 41886.8 | 20035.2 | 2.09 | 5592.05 | 4565.39 | 1.22 |
| 1.00 | 7689.44 | 5211.31 | 1.48 | 38156.5 | 19024.9 | 2.01 | 5245.27 | 4422.57 | 1.19 |
| 1.25 | 7061.61 | 4986.71 | 1.42 | 34477 | 17943.1 | 1.92 | 4898.96 | 4274.30 | 1.15 |
| 1.58 | 6447.95 | 4754.53 | 1.36 | 30920.7 | 16794.5 | 1.84 | 4547.48 | 4115.86 | 1.10 |
| 1.99 | 5829.38 | 4503.61 | 1.29 | 27480.8 | 15610.1 | 1.76 | 4203.40 | 3955.20 | 1.06 |
| 2.50 | 5232.15 | 4245.34 | 1.23 | 24218.4 | 14395.1 | 1.68 | 3870.93 | 3801.17 | 1.02 |
| 3.15 | 4661.86 | 3985.1 | 1.17 | 21145.3 | 13186.1 | 1.60 | 3543.47 | 3641.46 | 0.97 |
| 3.96 | 4122.36 | 3722.59 | 1.11 | 18291.9 | 12002.7 | 1.52 | 3229.86 | 3482.88 | 0.93 |
| 4.99 | 3615.3 | 3462.12 | 1.04 | 15725.2 | 10891.8 | 1.44 | 2921.97 | 3317.46 | 0.88 |
| 6.28 | 3145.25 | 3204.88 | 0.98 | 13417.7 | 9842.15 | 1.36 | 2633.65 | 3164.85 | 0.83 |
| 7.91 | 2712.73 | 2952.32 | 0.92 | 11380.6 | 8860.65 | 1.28 | 2357.33 | 3003.88 | 0.78 |
| 9.96 | 2322.22 | 2709.03 | 0.86 | 9393.87 | 7830.29 | 1.20 | 2096.82 | 2842.24 | 0.74 |
| 12.53 | 1976.47 | 2480.43 | 0.80 | 8041.68 | 7092.16 | 1.13 | 1855.43 | 2680.33 | 0.69 |
| 15.78 | 1676.06 | 2270.45 | 0.74 | 6800.04 | 6388.71 | 1.06 | 1635.64 | 2519.77 | 0.65 |
| 19.86 | 1422.46 | 2085.33 | 0.68 | 5718.69 | 5743.78 | 1.00 | 1438.62 | 2362.61 | 0.61 |
| 25.01 | 1211.93 | 1925.18 | 0.63 | 4698.89 | 5082.9 | 0.92 | 1265.03 | 2210.33 | 0.57 |
| 31.48 | 1041.53 | 1792.73 | 0.58 | 4049.41 | 4660.93 | 0.87 | 1114.98 | 2065.09 | 0.54 |
| 39.64 | 906.333 | 1688.18 | 0.54 | 3350.94 | 4216.29 | 0.79 | 986.44 | 1930.10 | 0.51 |
| 49.90 | 799.303 | 1610.22 | 0.50 | 2827.47 | 3881.62 | 0.73 | 879.63 | 1810.42 | 0.49 |
| 62.82 | 712.601 | 1553.63 | 0.46 | 2402.63 | 3631.71 | 0.66 | 791.96 | 1711.83 | 0.46 |
| 79.08 | 638.076 | 1511.66 | 0.42 | 2050.6 | 3453.85 | 0.59 | 719.82 | 1640.26 | 0.44 |
| 99.57 | 569.146 | 1476.47 | 0.39 | 1762.2 | 3362.4 | 0.52 | 658.18 | 1596.62 | 0.41 |

As shown in Table 5 and illustrated in FIG. 3, several of the strain percentages for both the 1.5% fumed silica +1.5% sorbitan sebacate behenate polymer and the 2.5% fumed silica +2.5% sorbitan sebacate behenate polymer formulations yielded a structural parameter (G'/G") of greater than or equal to 1. Based on this, it can be inferred that the solid powder ingredients will stay homogenously suspended in the hydrophobic matrix, and therefore both of the tested formulations will have enhanced shelf stability.

What is claimed is:

1. A tooth whitening composition comprising:
   at least one hydrophobic polymer carrier;
   fumed silica;
   sorbitan sebacate behenate polymer; and
   at least one whitening agent;
   wherein the composition possesses an elastic modulus (G') and a viscous modulus (G");
   wherein the ratio of the elastic modulus (G') to the viscous modulus (G") of the tooth whitening composition is greater than or equal to 1 as determined by a strain sweep test.

2. The tooth whitening composition according to claim 1, wherein the hydrophobic polymer carrier is a silicone pressure sensitive adhesive.

3. The tooth whitening composition according to claim 1, wherein the hydrophobic polymer carrier is a polydiorganosiloxane.

4. The tooth whitening composition according to claim 1, wherein the hydrophobic polymer carrier is present in the tooth whitening composition in an amount ranging from about 20% to about 80% by weight relative to the total weight of the composition.

5. The tooth whitening composition according to claim 1, wherein the at least one whitening agent is hydrogen peroxide.

6. The tooth whitening composition according to claim 5, wherein the hydrogen peroxide is present in the tooth whitening composition in an amount ranging from about 0.1% to about 10% by weight relative to the total weight of the composition.

7. The tooth whitening composition according to claim 1, wherein the composition is anhydrous.

8. The tooth whitening composition according to claim 1, wherein the composition is substantially free of polyethylene.

9. The tooth whitening composition according to claim 1, wherein the fumed silica is present in the tooth whitening composition in an amount ranging from about 1.5% to about 3% by weight relative to the total weight of the composition.

10. The tooth whitening composition according to claim 1, wherein the sorbitan sebacate behenate polymer is present in the tooth whitening composition in an amount ranging from about 1.5% to about 3% by weight relative to the total weight of the composition.

11. The tooth whitening composition according to claim 1, further comprising mineral oil.

12. The tooth whitening composition according to claim 1, further comprising polyvinylpyrrolidone.

13. A method for whitening a surface of a tooth comprising:
    contacting the surface of a tooth with the tooth whitening composition of claim 1 for a duration of time sufficient to effect whitening of the surface of the tooth.

14. The method according to claim 13, wherein the duration of time ranges from about 1 minute to about 45 minutes.

15. The method according to claim 13, wherein the tooth whitening composition is substantially free of polyethylene.

16. The method according to claim 13, wherein the tooth whitening composition further comprises mineral oil.

17. The method according to claim 13, wherein the tooth whitening composition further comprises polyvinylpyrrolidone.

18. A method for making the tooth whitening composition of claim 1 comprising: combining the at least one hydrophobic polymer carrier, the fumed silica, the sorbitan sebacate behenate polymer, and the at least one whitening agent; and mixing the at least one hydrophobic polymer carrier, the fumed silica, the sorbitan sebacate behenate polymer, and the at least one whitening agent to form a homogenous dispersion.

19. The method according to claim 18, wherein the at least one whitening agent is hydrogen peroxide.

20. The method according to claim 18, further comprising mixing at least one of flavoring agents, sweeteners, desensitizing agents, anti-microbial agents, anti-caries agents, anti-calculus agents, anti-inflammatory agents, vitamins, pigments and coloring agents, and preservatives.

* * * * *